(12) United States Patent
Watanabe

(10) Patent No.: US 8,636,886 B2
(45) Date of Patent: Jan. 28, 2014

(54) GAS SENSOR ELEMENT AND METHOD OF MANUFACTURING THE SAME

(75) Inventor: Atsushi Watanabe, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 104 days.

(21) Appl. No.: 13/071,916

(22) Filed: Mar. 25, 2011

(65) Prior Publication Data

US 2011/0240469 A1    Oct. 6, 2011

(30) Foreign Application Priority Data

Mar. 31, 2010    (JP) ................. 2010-080374

(51) Int. Cl.
G01N 27/407    (2006.01)

(52) U.S. Cl.
USPC .............. 204/429; 204/410; 205/783.5

(58) Field of Classification Search
USPC .......... 204/410, 411, 421–429; 205/781, 205/783.5–785, 787; 73/23.31, 23.32; 156/89.11–89.28
See application file for complete search history.

(56) References Cited

U.S. PATENT DOCUMENTS

| | | | |
|---|---|---|---|
| 4,097,353 A | 6/1978 | Kishida et al. | |
| 4,836,906 A | 6/1989 | Yamada et al. | |
| 2002/0106306 A1 | 8/2002 | Wang et al. | |
| 2005/0034986 A1 * | 2/2005 | Scheer et al. | 204/426 |
| 2005/0126910 A1 | 6/2005 | Sakon et al. | |
| 2006/0231397 A1 | 10/2006 | Nakagaki et al. | |
| 2007/0080061 A1 | 4/2007 | Gorte et al. | |
| 2008/0156644 A1 | 7/2008 | Suzuki et al. | |
| 2009/0239053 A1 * | 9/2009 | Shindo et al. | 428/221 |

FOREIGN PATENT DOCUMENTS

| | | |
|---|---|---|
| DE | 10 2004 057 203 A1 | 6/2005 |
| JP | 62-187245 | 8/1987 |
| JP | 63-167260 | 7/1988 |
| JP | 01-227955 | 9/1989 |
| JP | 2563953 | 9/1996 |
| JP | 2005-283240 | 10/2005 |
| JP | 2008-164411 A1 | 7/2008 |

OTHER PUBLICATIONS

Jing-Shan Do, et al., "Amperometric NO Gas Sensor in the Presence of Diffusion Barrier: Selectivity, Mass Transfer of NO and Effect of Temperature," Sensors and Actuators, vol. 86, No. 1, Aug. 30, 2002, pp. 98-105.

V. Schüle, et al., "Soot Sensor Based on Porous Solid Electrolyte Cell," Sensors and Actuators, vol. 16, No. 1-3, Oct. 1, 2003, pp. 249-251.

Japanese Office Action, dated Apr. 10, 2012 ( 2 Pages).

* cited by examiner

Primary Examiner — J. Christopher Ball
(74) Attorney, Agent, or Firm — Burr & Brown, PLLC

(57) ABSTRACT

A gas sensor element includes a base member comprising a plurality of laminated solid electrolyte layers, and having a space that communicates with the outside of the gas sensor element and allows introduction of the gas to be measured into the gas sensor element, and a porous measurement electrode that is formed on a surface of the space inside the base member, and is covered with a porous measurement electrode protective layer, wherein an average pore size A of the measurement electrode and an average pore size B of the measurement electrode protective layer satisfy the relationship "$0.05 \leq B/A \leq 0.9$", the measurement electrode has an average pore size of 0.5 to 15 μm, and the measurement electrode protective layer has an average pore size of 0.05 to 9 μm, a porosity of 5 to 50%, and a thickness of 10 to 200 μm.

9 Claims, 1 Drawing Sheet

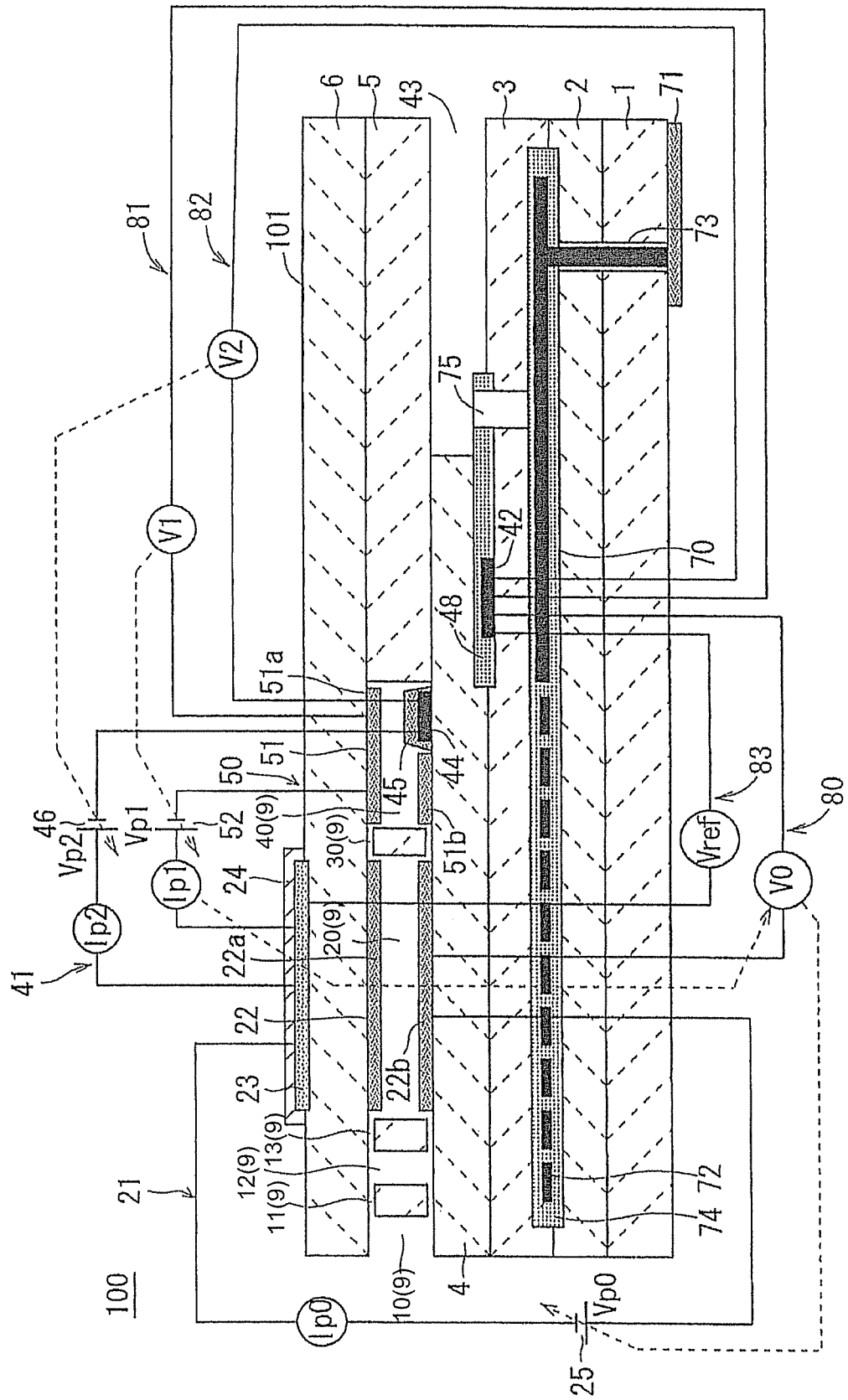

GAS SENSOR ELEMENT AND METHOD OF MANUFACTURING THE SAME

FIELD OF THE INVENTION

1. Background of the Invention

The present invention relates to a gas sensor element that is used to measure the concentration of a specific gas component in a gas to be measured, and a method of manufacturing the same.

2. Description of Related Art

A gas sensor element that is used to measure the concentration of a specific gas component in a gas to be measured may include a base member comprising a plurality of laminated solid electrolyte layers, and having a space that communicates with the outside of the gas sensor element and allows introduction of the gas to be measured into the gas sensor element, and a porous measurement electrode that is formed on the surface of the space inside the base member, and is covered with a porous measurement electrode protective layer. The measurement electrode protective layer of such a gas sensor element traps an electrode poisoning substance contained in the gas to be measured so that the poisoning substance does not adhere to the measurement electrode, and also functions as a diffusion-controlled section that limits the amount of a specific gas component (i.e., target gas component whose concentration is to be measured) contained in the gas to be measured that reaches the measurement electrode. A number of pores that allow the gas to be measured to pass there through are formed in the measurement electrode protective layer so that an excellent diffusion-controlled capability can be obtained.

For example, JP-A-S62-187245, JP-A-H1-227955, JP-A-S63-167260, and JP-B-2563953 disclose a conventional sensor element having a structure in which the measurement electrode protective layer is formed on the surface of the measurement electrode.

By the way, in the case that the poisoning substance enters the sensor element being contained in the gas to be measured, the poisoning substance can be effectively trapped by the measurement electrode protective layer before the poisoning substance reaches the measurement electrode. However, in the case that the gas to be measured contains water (e.g., exhaust gas discharged from an engine), and the poisoning substance contained in the gas to be measured enters the sensor element in a solution state, the effective trap of the poisoning substance by the measurement electrode protective layer would become difficult depending on the relationship between the pore size of the measurement electrode and the pore size of the measurement electrode protective layer.

Specifically, when the pore size of the measurement electrode is smaller than that of the measurement electrode protective layer, the poisoning substance-containing solution that has adhered to the measurement electrode protective layer reaches into the pores in the measurement electrode having smaller pore size due to a capillary force. A gas sensor element is normally driven in a state in which the gas sensor element is heated by a heating means (e.g., heater). Therefore, since the solution that has reached into the pores in the measurement electrode is dried to deposit, the surface of the measurement electrode may be covered with the deposited poisoning substance, or the pores in the measurement electrode may be clogged. As a result, the measurement electrode may deteriorate to reduce the sensitivity of the sensor element.

In the sensor elements disclosed in JP-A-S62-187245, JP-A-H1-227955, JP-A-S63-167260, and JP-B-2563953, since the relationship between the pore size of the measurement electrode and the pore size of the measurement electrode protective layer has not been considered, there is a fear that the effective trap of the poisoning substance by the measurement electrode protective layer becomes difficult as mentioned above, and this results in the reduction in the sensitivity of the sensor element.

SUMMARY OF THE INVENTION

The present invention has been made in view of such a conventional situation. An object of the present invention is to provide a highly durable gas sensor element that prevents a situation in which a poisoning substance-containing solution that has adhered to the measurement electrode protective layer reaches into the pores in the measurement electrode, and suppresses the reduction in sensitivity due to a deterioration in the measurement electrode and clogging of the pores in the measurement electrode caused by the poisoning substance, and a method of manufacturing the same.

The above object can be achieved by the following gas sensor element and method of manufacturing the same.

[1] A gas sensor element being used to measure the concentration of a specific gas component in a gas to be measured, and including: a base member comprising a plurality of laminated solid electrolyte layers, and having a space that communicates to the outside of the gas sensor element and allows introduction of the gas to be measured into the gas sensor element; and a porous measurement electrode that is formed on a surface of the space inside the base member, and is covered with a porous measurement electrode protective layer, wherein an average pore size A of the measurement electrode and an average pore size B of the measurement electrode protective layer satisfy the relationship "$0.05 \leq B/A \leq 0.9$"; the measurement electrode has an average pore size of 0.5 to 15 μm; and the measurement electrode protective layer has an average pore size of 0.05 to 9 μm, a porosity of 5 to 50%, and a thickness of 10 to 200 μm.

[2] The gas sensor element according to [1], wherein the average pore size A of the measurement electrode and the average pore size B of the measurement electrode protective layer satisfy the relationship "$0.1 < B/A < 0.65$".

[3] The gas sensor element according to [1] or [2], wherein the measurement electrode protective layer is made of at least one material selected from the group consisting of yttria-partially stabilized zirconia, calcia-partially stabilized zirconia, yttria-stabilized zirconia, calcia-stabilized zirconia, α-alumina, $Al_2O_3 \cdot MgO$ spinel, mullite, yttria, magnesia, and cordierite.

[4] A method of manufacturing the gas sensor element according to any one of [1] to [3], the method including: printing the measurement electrode on a surface of an unfired body of a base member, which forms solid layers when fired, using a measurement electrode paste that includes a constituent material for the measurement electrode, and printing the measurement electrode protective layer on the unfired body to cover the measurement electrode using a measurement electrode protective layer paste that includes a ceramic aggregate and a pore former to form a printed laminate body; and firing the printed laminate body, wherein the printed laminate body is fired at 1200 to 1500° C.

[5] The method according to [4], wherein the measurement electrode paste includes a pore former.

[6] The method according to [4] or [5], wherein the ceramic aggregate included in the measurement electrode protective layer paste is at least one type of ceramic particles selected from the group consisting of yttria-partially stabilized zirconia, calcia-partially stabilized zirconia, yttria-stabilized zirconia, calcia-stabilized zirconia, α-alumina, Al$_2$O$_3$.MgO spinel, mullite, yttria, magnesia, and cordierite.

It is to be noted that the porosity of the measurement electrode protective layer refers to a value obtained by polishing the cross section of the measurement electrode protective layer, binarizing the aggregate parts and the pore parts in black and white by analyzing a photograph of the polished surface obtained using a scanning electron microscope (SEM) to calculate the area of the pore parts, and calculating the ratio of the area of the pore parts to the total area of the aggregate parts and the pore parts to calculate the porosity in the present invention.

Moreover, the respective average pore sizes for both the measurement electrode and the measurement electrode protective layer of the sensor element cannot be directly measured. Therefore, a formed measurement electrode sheet having the same thickness as that of the measurement electrode formed in the sensor element is produced using the measurement electrode paste, and a formed measurement electrode protective layer sheet having the same thickness as that of the measurement electrode protective layer formed in the sensor element is produced using the measurement electrode protective layer paste. The sheets are fired at the same temperature as that employed for the sensor element to obtain a fired measurement electrode sheet and a fired measurement electrode protective layer sheet. The average pore sizes of the fired sheets are measured using a mercury porosimeter, and taken as respective the average pore sizes for the measurement electrode and the measurement electrode protective layer in the present invention.

According to the gas sensor element of the present invention, since the average pore size of the measurement electrode and the average pore size of the measurement electrode protective layer satisfy the given relationship, the capillary force in the measurement electrode protective layer increases as compared with the capillary force in the measurement electrode, so that the reaching of a poisoning substance-containing solution to the measurement electrode can be prevented effectively even in a case that the poisoning substance-containing solution adheres onto the measurement electrode protective layer. As a result, a reduction in sensitivity due to poisoning of the surface of the measurement electrode and clogging of the pores in the measurement electrode caused by the poisoning substance can be suppressed, and high durability is achieved. Moreover, the method of manufacturing a gas sensor element of the present invention can produce a gas sensor element that exhibits high durability against a poisoning substance.

BRIEF DESCRIPTION OF THE DRAWINGS

FIG. 1 is a cross-sectional view showing an example of one embodiment of a gas sensor element according to the present invention.

EXPLANATION OF NUMERICAL SYMBOLS

1: a first substrate layer, 2: a second substrate layer, 3: a third substrate layer, 4: a first solid electrolyte layer, 5: a spacer layer, 6: a second solid electrolyte layer, 9: space, 10: a gas inlet, 11: a first diffusion-controlled section, 12: a buffer space, 13: a second diffusion-controlled section, 20: a first internal space, 21: a main pump cell, 22: an inner pump electrode (22a: an upper inner pump electrode, 22b: an under inner pump electrode), 23: an outer pump electrode, 24: an outer pump electrode protective layer (an outer circumferential surface protective layer), 25: variable source, 30: a third diffusion-controlled section, 40: a second internal space, 41: a measurement pump cell, 42: a reference electrode, 43: a reference gas introduction space, 44: measurement electrode, 45: a measurement electrode protective layer (a fourth diffusion-controlled section), 46: variable source, 48: an air introduction layer, 50: an auxiliary pump cell, 51: an auxiliary pump electrode (51a: an upper auxiliary pump electrode, 51b: an under auxiliary pump electrode), 52: variable source, 70: a heater, 71: a heater electrode, 72: resistance heating elements, 73: a thorough-hole, 74: a heater insulating layer, 75: a pressure diffusion hole, 80: a partial-pressure-of-oxygen detection sensor cell for controlling a main pump, 81: a partial-pressure-of-oxygen detection sensor cell for controlling an auxiliary pump, 82: a partial-pressure-of-oxygen detection sensor cell for controlling a measurement pump, 83: a partial-pressure-of-oxygen detection sensor cell outside of a sensor, 100: a gas sensor element, 101: a base member.

DETAILED DESCRIPTION OF THE INVENTION

Exemplary embodiments of the present invention are described below. Note that the present invention is not limited to the following embodiments. Various alternations, modifications and improvements may be made of the following embodiments without departing from the scope of the present invention based on the knowledge of a person having an ordinary skill in the art.

As mentioned above, a gas sensor element of the present invention is used to measure the concentration of a specific gas component in a gas to be measured, and includes: a base member comprising a plurality of laminated solid electrolyte layers, and having a space that communicates with the outside of the gas sensor element and allows introduction of the gas to be measured into the gas sensor element; and a porous measurement electrode that is formed on a surface of the space inside the base member, and is covered with a porous measurement electrode protective layer. The major features of the present invention are that an average pore size A of the measurement electrode and an average pore size B of the measurement electrode protective layer satisfy the relationship "$0.05 \leq B/A \leq 0.9$"; the measurement electrode has an average pore size of 0.5 to 15 μm; and the measurement electrode protective layer has an average pore size of 0.05 to 9 μm, a porosity of 5 to 50%, and a thickness of 10 to 200 μm.

FIG. 1 is a cross-sectional view showing an example of one embodiment of a gas sensor element according to the present invention. A gas sensor element 100 shown in FIG. 1 is a NOx sensor element that detects the NOx concentration in a gas to be measured, and includes a base member 101 comprising a first substrate layer 1, a second substrate layer 2, a third substrate layer 3, a first solid electrolyte layer 4, a spacer layer 5, and a second solid electrolyte layer 6 being laminated in this order, and each of them are made of an oxygen ion-conductive solid electrolyte layer (e.g., zirconia (ZrO$_2$)). It is to be noted that the structure and the operation principle of such a gas sensor element 100 are known in the art (see JP-A-2008-164411, for example).

In the gas sensor element 100, the space 9 may includes a gas inlet 10, a first diffusion-controlled section 11, a buffer space 12, a second diffusion-controlled section 13, a first internal space 20, a third diffusion-controlled section 30, and a second internal space 40 which are formed in this order between the under surface of the second solid electrolyte layer 6 and the upper surface of the first solid electrolyte layer 4 to communicate in the direction from the end (left end in FIG. 1) to the inside of the gas sensor element 100. The gas inlet 10, the buffer space 12, the first internal space 20, and the second internal space 40 are spaces formed by processing the spacer layer 5. The upper side of these spaces is partitioned by the under surface of the second solid electrolyte layer 6, the under side of these spaces is partitioned by the upper surface of the first solid electrolyte layer 4, and the side of these spaces is partitioned by the wall surface of the processed space of spacer layer 5. Each of the first diffusion-controlled section 11, the second diffusion-controlled section 13, and the third diffusion-controlled section 30 is formed by two oblong slits (i.e., the direction perpendicular to the sheet coincides with the longitudinal direction of the opening). It is to be noted that an area from the gas inlet 10 to the second internal space 40 may be referred to as a gas passage (gas circulation section).

A reference gas introduction space 43 is formed at a position away from the end of the gas sensor element 100 as compared with the gas passage. This reference gas introduction space 43 is formed by processed the first solid electrolyte layer 4. The upper side of the reference gas introduction space 43 is partitioned by the under surface of the spacer layer 5, the under side of the reference gas introduction space 43 is partitioned by the upper surface of the third substrate layer 3, and the side of the reference gas introduction space 43 is partitioned by the wall surface of the processed space of the first solid electrolyte layer 4. Air is introduced into the reference gas introduction space 43 as a reference gas when measuring the NOx concentration, for example. An air introduction layer 48 made of porous alumina is provided between the first solid electrolyte layer 4 and the third substrate layer 3. The reference gas is introduced into the air introduction layer 48 via the reference gas introduction space 43. The air introduction layer 48 is also formed to cover a reference electrode 42. The reference electrode 42 is formed between the upper surface of the third substrate layer 3 and the under surface of the first solid electrolyte layer 4. As above mentioned, the air introduction layer 48 led to the reference gas introduction space 43 is provided to surround the reference electrode 42. Moreover, the oxygen concentration (partial pressure of oxygen) in the first internal space 20 and the second internal space 40 can be measured using the reference electrode 42 (described later).

The first internal space 20 is provided as a space for adjusting the partial pressure of oxygen in the gas to be measured introduced via the second diffusion-controlled section 13. This partial pressure of oxygen is adjusted by operating a main pump cell 21. The main pump cell 21 is an electrochemical pump cell that includes an inner pump electrode 22 provided in the first internal space 20 and fanned in the shape of a tunnel, an outer pump electrode 23 provided on the surface of the second solid electrolyte layer 6 opposite to the inner pump electrode 22 side, and the second solid electrolyte layer 6 intervened between the electrodes 22 and 23. The inner pump electrode 22 and the outer pump electrode 23 are formed as porous cermet electrodes (e.g., $Pt/ZrO_2$ cermet electrode containing 1% of Au).

The outer pump electrode 23 is covered with an outer pump electrode protective layer (outer circumferential surface protective layer) 24. The outer pump electrode protective layer 24 is made of a porous body having a thickness of 10 to 200 μm. The material for the outer pump electrode protective layer 24 is not particularly limited insofar as the material is a porous body. For example, the material of the outer pump electrode protective layer 24 is preferably alumina porous body, zirconia porous body (partially stabilized zirconia or fully stabilized zirconia), spinel porous body, cordierite porous body, or the like. These materials may optionally contain sodium, potassium, calcium, magnesium, barium, aluminum, zirconium, silicon, and the like.

The main pump cell 21 is configured so that oxygen contained in the first internal space 20 can be removed to the outer space, or introduced into the first internal space 20 by causing a pump current Ip0 to flow between the inner pump electrode 22 and the outer pump electrode 23 in the positive direction or the negative direction by applying a desired pump voltage Vp0 between the inner pump electrode 22 and the outer pump electrode 23.

Moreover, in order to detect the oxygen concentration (partial pressure of oxygen) in the first internal space 20, an electrochemical sensor cell (i.e., partial-pressure-of-oxygen detection sensor cell 80 for controlling the main pump) is constituent by the inner pump electrode 22, the second solid electrolyte layer 6, the spacer layer 5, the first solid electrolyte layer 4, the third substrate layer 3, and the reference electrode 42. The oxygen concentration (partial pressure of oxygen) in the first internal space 20 can be detected by measuring an electromotive force V0 of the partial-pressure-of-oxygen detection sensor cell 80. Furthermore, the pump current Ip0 is controlled by feedback-controlling a variable source 25 (voltage Vp0) so that the electromotive force V0 is constant. This makes it possible to maintain the oxygen concentration in the first internal space 20 at a constant value.

The second internal space 40 is a space for performing a process for measuring the NOx concentration in the gas to be measured introduced via the third diffusion-controlled section 30. The third diffusion-controlled section 30 applies a given diffusion resistance to the gas to be measured in which the oxygen concentration (partial pressure of oxygen) has been controlled in the first internal space 20 due to the operation of the main pump cell 21, and guides the gas to be measured to the second internal space 40.

In the second internal space 40, the partial pressure of oxygen in the gas to be measured that has been adjusted in oxygen concentration (partial pressure of oxygen) contained in the atmosphere in the first internal space 20 beforehand and introduced via the third diffusion-controlled section 30 is further adjusted using an auxiliary pump cell 50. This makes it possible to accurately maintain the oxygen concentration in the second internal space 40 at a constant value to be able to measure the NOx concentration with high accuracy.

The auxiliary pump cell 50 is an auxiliary electrochemical pinup cell that includes an auxiliary pump electrode 51 that is provided in the second internal space 40 and formed in the shape of a tunnel, the outer pump electrode 23, and the second solid electrolyte layer 6.

The auxiliary pump cell 50 is configured so that oxygen contained in the atmosphere in the second internal space 40 can be removed to the outer space, or can be introduced into the second internal space 40 by applying a desired voltage Vp1 between the auxiliary pump electrode 51 and the outer pump electrode 23.

Moreover, in order to control the partial pressure of oxygen contained in the atmosphere in the second internal space 40, an electrochemical sensor cell (i.e., partial-pressure-of-oxygen detection sensor cell 81 for controlling the auxiliary pump) is formed by the auxiliary pump electrode 51, the reference electrode 42, the second solid electrolyte layer 6, the spacer layer 5, the first solid electrolyte layer 4, and the third substrate layer 3. This partial-pressure-of-oxygen detection sensor cell 81 detects an electromotive force V1 between the auxiliary pump electrode 51 and the reference electrode 42. The auxiliary pump cell 50 performs a pumping operation using a variable source 52 (voltage Vp1) that is voltage-controlled based on this electromotive force V1. This makes it possible to control the partial pressure of oxygen contained in the atmosphere in the second internal space 40 to such a low partial pressure that the NOx concentration measurement is not substantially affected. In parallel, a pump current Ip1 of the auxiliary pump cell 50 is also used to control the electromotive force V0 of the partial-pressure-of-oxygen detection sensor cell 80 for controlling the main pump. The slope (gradient) of the partial pressure of oxygen in the gas to be measured introduced into the second internal space 40 from the third diffusion-controlled section 30 is thus controlled to be always constant.

A measurement pump cell 41 measures the NOx concentration in the gas to be measured in the second internal space 40. The measurement pump cell 41 is an electrochemical pump cell that includes a measurement electrode 44, the outer pump electrode 23, the second solid electrolyte layer 6, the spacer layer 5, and the first solid electrolyte layer 4. The measurement electrode 44 is provided on the upper surface of the first solid electrolyte layer 4 that faces the second internal space 40, and is spaced away from the third diffusion-controlled section 30. This measurement electrode 44 is a porous cermet electrode that is almost rectangular when viewed from above. The measurement electrode 44 also functions as a NOx reduction catalyst that reduces NOx existed in the atmosphere in the second internal space 40. Furthermore, the measurement electrode 44 is covered with a measurement electrode protective layer 45. The measurement electrode protective layer 45 is formed of a ceramic porous body. The measurement electrode protective layer 45 functions as a protective film for the measurement electrode 44, and also functions as a diffusion-controlled section that limits the amount of NOx that flows into the measurement electrode 44.

This measurement pump cell 41 removes oxygen produced by decomposition of NOx contained in the atmosphere around the measurement electrode 44, and can detect the amount of oxygen as a pump current Ip2 that flows between the measurement electrode 44 and the outer pump electrode 23.

Moreover, in order to detect the partial pressure of oxygen around the measurement electrode 44, an electrochemical sensor cell (i.e., partial-pressure-of-oxygen detection sensor cell 82 for controlling the measurement pump) is formed by the second solid electrolyte layer 6, the spacer layer 5, the first solid electrolyte layer 4, the third substrate layer 3, the measurement electrode 44, and the reference electrode 42. A variable source 46 (voltage Vp2) of the measurement pump cell 41 is controlled based on an electromotive force V2 detected by the partial-pressure-of-oxygen detection sensor cell 82 for controlling the measurement pump.

The gas to be measured introduced into the second internal space 40 reaches the measurement electrode 44 via the porous measurement electrode protective layer 45 under such a situation in which partial pressure of oxygen is controlled. NOx contained in the gas to be measured around the measurement electrode 44 is reduced to produce oxygen ($2NO \rightarrow N_2 + O_2$). This oxygen produced is pumped by the measurement pump cell 41. In this case, the voltage Vp2 of the variable source 46 is controlled so that the electromotive force V2 detected by the Partial-pressure-of-oxygen detection sensor cell 82 for controlling the measurement pump is constant. Since the amount of oxygen produced around the measurement electrode 44 is proportional to the NOx concentration in the gas to be measured, the NOx concentration in the gas to be measured is calculated using the pump current Ip2 of the measurement pump cell 41. The specific procedure for developing the NOx concentration is as follows. That is, the pump current Ip2 when introducing a sample gas that does not contain NOx is referred to as an offset current. A pump current difference $\Delta Ip2$ is calculated by subtracting the offset current from the pump current Ip2 detected when introducing the actual gas to be measured, and the NOx concentration is calculated from the amount of oxygen corresponding to the pump current difference $\Delta Ip2$.

In the gas sensor element (NOx sensor element) 100 having the above configuration, the gas to be measured in which the partial pressure of oxygen is always maintained at a constant low value (i.e., a value at which the NOx concentration measurement is not substantially affected) by operating the main pump cell 21 and the auxiliary pump cell 50 is applied to the measurement pump cell 41. Therefore, oxygen that is produced due to reduction of NOx roughly in proportion to the NOx concentration in the gas to be measured is removed out from the measurement pump cell 41, and the NOx concentration in the gas to be measured can be determined (detected) based on the pump current Ip2 which is flowed due to thereon.

The electrochemical sensor cell 83 is also formed by the second solid electrolyte layer 6, the spacer layer 5, the first solid electrolyte layer 4, the third substrate layer 3, the outer pump electrode 23, and the reference electrode 42. The partial pressure of oxygen in the gas to be measured outside the sensor can be detected based on the electromotive force Vref obtained by this sensor cell 83.

A heater 70 is positioned between the second substrate layer 2 and the third substrate layer 3. This heater 70 heats the gas sensor element 100 to keep it warm (i.e., adjusts the temperature of the gas sensor element 100) in order to improve the oxygen ion conductivity of the solid electrolyte that forms each layer. Moreover, the heater 70 includes a heater electrode 71, a resistance heating element 72, and a heater insulating layer 74. Furthermore, the heater 70 communicates with the reference gas introduction space 43 via a pressure diffusion hole 75 passed through the third substrate layer 3 to absorb the pressure increase inside the heater 70. The heater electrode 71 is in contact with the under surface of the first substrate layer 1. This heater electrode 71 is connected to an external source (not shown) to supply power to the resistance heating element 72 from the outside. The resistance heating element 72 is connected to the heater electrode 71 via a through-hole 73 processed at the first substrate 1 and the second substrate 2. This resistance heating element 72 is buried over the entire area under the first internal space 20 and the second internal space 40. So, the entire gas sensor element 100 can be heated to a temperature at which the solid electrolyte is activated. The heater insulating layer 74 is formed on the upper and the under surface of the resistance heating element 72 using an insulator (e.g., alumina).

The gas sensor element of the present invention is configured so that the average pore size A of the measurement electrode 44 and the average pore size B of the measurement electrode protective layer 45 satisfy the relationship "$0.05 \leq B/A \leq 0.9$" (preferably "$0.1 < B/A < 0.65$"). When the relationship "$0.05 \leq B/A \leq 0.9$" is satisfied, the reaching of a poisoning substance-containing solution to the measurement electrode can be prevented effectively even in a case that the poisoning substance-containing solution adheres onto the measurement electrode protective layer. Therefore, it is possible to prevent a deterioration in the measurement electrode and clogging of the pores due to the poisoning substance, to maintain the sensor sensitivity. Specifically, when the average pore size of the measurement electrode protective layer 45 that covers the measurement electrode 44 is smaller than the average pore size of the measurement electrode 44 by a given ratio or more, a solution including a poisoning substance that has adhered to the measurement electrode protective layer 45 is concentrated in the pores in the measurement electrode protective layer 45 having a small pore size due to capillary force, and rarely invades in the pores in the measurement electrode 44.

It is to be noted that when the ratio B/A is less than 0.05, the pores in the measurement electrode protective layer 45 may be easily clogged by the poisoning substance included in the solution since the average pore size of the measurement electrode protective layer 45 is too small. Therefore, the sensor sensitivity may decrease within a short time. On the other hand, when the ratio B/A exceeds 0.9, a solution including a poisoning substance that has adhered to the measurement electrode protective layer 45 may easily reach into the pores in the measurement electrode 44. Therefore, the sensor sensitivity may decrease.

In the gas sensor element of the present invention, the average pore size of the measurement electrode 44 is 0.5 to 15 μm, preferably 0.75 to 10 μm, and more preferably 1 to 5 μm. When the average pore size of the measurement electrode 44 is less than 0.5 μm, a poisoning substance may easily reach the measurement electrode 44 from the measurement electrode protective layer 45 due to an increase in capillary force of the measurement electrode 44. Therefore, the sensor sensitivity may decrease. On the other hand, when the average pore size of the measurement electrode 44 exceeds 15 μm, cracks may occur in the measurement electrode 44 due to a decrease in strength.

Moreover, in the gas sensor element of the present invention, the average pore size of the measurement electrode protective layer 45 is 0.05 to 9 μm, preferably 0.25 to 7 μm, and more preferably up to 5 μm. When the average pore size of the measurement electrode protective layer 45 is less than 0.05 μm, the pores in the measurement electrode protective layer 45 may be easily clogged. Therefore, the sensor sensitivity may decrease within a short time. On the other hand, when the average pore size of the measurement electrode protective layer 45 exceeds 9 μm, cracks may occur in the measurement electrode protective layer 45 due to a decrease in strength.

Furthermore, in the gas sensor element of the present invention, the porosity of the measurement electrode protective layer 45 is 5 to 50%, preferably 8 to 40%, and more preferably 10 to 30%. When the porosity of the measurement electrode protective layer 45 is less than 5%, the pores in the measurement electrode protective layer 45 may not communicate. As a result, the gas sensor element does not function as sensor since the gas to be measured may not reach the measurement electrode 44. On the other hand, when the porosity of the measurement electrode protective layer 45 exceeds 50%, cracks may occur in the measurement electrode protective layer 45 due to a decrease in strength.

Moreover, in the gas sensor element of the present invention, the thickness of the measurement electrode protective layer 45 is 10 to 200 μm, preferably 15 to 150 μm, and more preferably 20 to 100 μm. When the thickness of the measurement electrode protective layer 45 is less than 10 μm, the tolerable amount till the pores in the measurement electrode protective layer 45 are clogged due to poisoning substance may be small. Therefore, the sensor sensitivity may reduce. On the other hand, when the thickness of the measurement electrode protective layer 45 exceeds 200 μm, cracks may occur in the measurement electrode protective layer 45.

In the gas sensor element of the present invention, the ceramic material constituting the measurement electrode protective layer 45 is not particularly limited, but is preferably at least one material selected from the group consisting of yttria-partially stabilized zirconia, calcia-partially stabilized zirconia, yttria-stabilized zirconia, calcia-stabilized zirconia, α-alumina, $Al_2O_3 \cdot MgO$ spinel, mullite, yttria, magnesia, and cordierite.

Note that a gas component in the gas to be measured of which the concentration is measured using the gas sensor element of the present invention is not particularly limited. The gas sensor element of the present invention may intend a various gas sensor element such as a NOx sensor element that measures the NOx concentration, or an $O_2$ sensor element that measures the $O_2$ concentration.

Next, a method of manufacturing a gas sensor element of the present invention is described below. The method of manufacturing a gas sensor element of the present invention manufactures the gas sensor element of the present invention, and includes printing a measurement electrode on the surface of an unfired body of a base member, which forms solid layers when fired, using a measurement electrode paste that includes a material for the measurement electrode, and printing a measurement electrode protective layer on the unfired body to cover the measurement electrode using a measurement electrode protective layer paste that includes a ceramic aggregate and a pore former to form a printed laminate body (hereinafter may be referred to as "printing step"); and firing the printed laminate body (hereinafter may be referred to as "firing step"), wherein the printed laminate body is fired at 1200 to 1500° C.

For example, in the case of manufacturing the gas sensor element 100 shown in FIG. 1, firstly green sheets (unfired bodies) that respectively form the first substrate layer 1, the second substrate layer 2, the third substrate layer 3, the first solid electrolyte layer 4, the spacer layer 5, and the second solid electrolyte layer 6 upon firing (described later) are produced using an oxygen ion-conductive solid electrolyte material (e.g., zirconia).

Next, the outer pump electrode 23 is printed on the upper surface of the green sheet (green sheet for second solid electrolyte layer) that forms the second solid electrolyte layer 6 upon firing using an electrode paste that includes an electrode material, and the inner pump electrode 22a and the auxiliary pump electrode 51a are further printed on the under surface of the green sheet for second solid electrolyte layer using the electrode paste together with wires connected to each electrode. The outer pump electrode protective layer (outer circumferential surface protective layer) 24 is then printed to cover the outer pump electrode 23 using an outer circumferential surface protective layer paste. It is to be noted that, the electrode paste may include a pore former, if needed.

Likewise, the inner pump electrode 22b and the auxiliary pump electrode 51b are printed on the upper surface of the green sheet (green sheet for first solid electrolyte layer green sheet) that forms the first solid electrolyte layer 4 upon firing using an electrode paste that includes an electrode material, and the measurement electrode 44 is further printed using a measurement electrode paste that includes a material for the measurement electrode together with wires connected to each electrode. The measurement electrode protective layer 45 is then printed to cover the measurement electrode 44 using a measurement electrode protective layer paste that includes a ceramic aggregate and a pore former. The part of this green sheet is also punched to form the reference gas introduction space 43. It is to be noted that, the electrode paste and the measurement electrode paste may include a pore former, if needed.

Moreover, the gas inlet 10, the first internal space 20, and the second internal space 40 are formed by punching the corresponding portion of the green sheet (green sheet for spacer layer) that forms the spacer layer 5 when fired. And, an organic paste that includes a sublimation substance is printed on the parts of the upper surface and the under surface of the green sheet for spacer layer in order to form slits for the first diffusion-controlled section 11, the second diffusion-controlled section 13, and the third diffusion-controlled section 30. The printed organic paste is burned down during firing to form the first diffusion-controlled section 11, the second diffusion-controlled section 13, and the third diffusion-controlled section 30.

Furthermore, the reference electrode 42 is printed on the upper surface of the green sheet (green sheet for third substrate layer) that forms the third substrate layer 3 upon firing using an electrode paste that includes an electrode material together with wires connected to the reference electrode 42. The air introduction layer 48 is then formed to cover the reference electrode 42 using an air introduction layer paste that includes a material for the air introduction layer 48. The part of this green sheet is punched to form the pressure diffusion hole 75.

Moreover, the heater insulating layer 74 is printed on the upper surface of the green sheet (green sheet for second substrate layer) that forms the second substrate layer 2 upon firing using a resistance heating element paste and an insulating layer paste that includes an alumina material or the like so that the heater insulating layer 74 covers the resistance heating element 72. The part of this green sheet is further punched to form the through-hole 73, and a heater wire is then formed.

Furthermore, the heater electrode 71 is printed on the under surface of the green sheet (green sheet for first substrate layer) that forms the first substrate layer 1 upon firing using a heater electrode paste. The part of this green sheet is further punched to form the through-hole 73, and a heater wire is then formed.

Subsequently, the green sheet for first substrate layer, the green sheet for second substrate layer, the green sheet for third substrate layer, the green sheet for first solid electrolyte layer, the green sheet for spacer layer, and the green sheet for second solid electrolyte layer are then laminated, cut at the end as needed, and fired to obtain the gas sensor element 100.

In the method of manufacturing a gas sensor element of the present invention, the firing temperature is 1200 to 1500° C., preferably 1250 to 1450° C., and more preferably 1300 to 1400° C. When the firing temperature is less than 1200° C., the measurement electrode protective layer 45 may exhibit insufficient strength due to insufficient sintering. Therefore, cracks may easily occur in the measurement electrode protective layer 45. On the other hand, when the firing temperature exceeds 1500° C., the pores in the measurement electrode protective layer 45 may not communicate due to excessive sintering. As a result, the gas sensor element does not function as sensor since the gas to be measured may not reach the measurement electrode 44.

In the method of manufacturing a gas sensor element of the present invention, the measurement electrode paste used when printing the measurement electrode 44 includes a material for the measurement electrode 45, and is added a pore former for adjusting the pore characteristics, as needed. The material for the measurement electrode 45 is preferably a material that includes yttria-partially stabilized zirconia, platinum, and rhodium, for example.

In the method of manufacturing a gas sensor element of present the invention, the measurement electrode protective layer paste used when printing the measurement electrode protective layer 45 includes a ceramic aggregate, and a pore former for adjusting the pore characteristics. The ceramic aggregate is not particularly limited, but is preferably at least one type of ceramic particles selected from the group consisting of yttria-partially stabilized zirconia, calcia-partially stabilized zirconia, yttria-stabilized zirconia, calcia-stabilized zirconia, α-alumina, $Al_2O_3 \cdot MgO$ spinel, mullite, yttria, magnesia, and cordierite.

The pore former contained in the measurement electrode paste and the measurement electrode protective layer paste, an organic material or an inorganic material, is not limited. The pore size distribution of the measurement electrode and the measurement electrode protective layer can be controlled by adjusting the particle size distribution of the pore former Therefore, it is possible to control the average pore size of the measurement electrode and the average pore size of the measurement electrode protective layer to satisfy the requirements of the gas sensor element of the present invention (i.e., $0.05 \leq B/A \leq 0.9$, average pore size of measurement electrode: 0.5 to 15 μm, and average pore size of measurement electrode protective layer: 0.05 to 9 μm).

Moreover, the porosity of the measurement electrode protective layer after firing can be easily controlled (i.e., the desired porosity can be easily obtained) by adjusting the content of the pore former in the measurement electrode protective layer paste. Therefore, it is possible to control the porosity of the measurement electrode protective layer to satisfy the requirements of the gas sensor element of present the invention (i.e.; porosity of measurement electrode protective layer: 5 to 50%).

As is described above, the thickness of the measurement electrode protective layer of the gas sensor element of the present invention is 10 to 200 μm. The thickness of the measurement electrode protective layer can be easily controlled by determining the burning shrinkage rate of the measurement electrode protective layer paste used when printing the measurement electrode protective layer in advance, and adjusting the thickness of the printed measurement electrode protective layer taking account of the burning shrinkage rate.

EXAMPLES

The present invention is described below in more detail by way of examples. However, the present invention is not limited to the following examples.

Preparation of Measurement Electrode Protective Layer Paste

A measurement electrode protective layer paste used to manufacture gas sensor elements No. 1 to No. 39 shown in Tables 1 and 2 was prepared as follows. A ceramic aggregate made of a material for the measurement electrode protective layer shown in Tables 1 and 2 and a pore former made of a melamine-formaldehyde condensate having a particle size shown in Tables 1 and 2 were mixed in a ratio shown in Tables 1 and 2 to prepare a raw material powder. After the addition of a given amount of acetone (dispersion medium), the mixture was premixed to obtain a premixed liquid. An organic binder solution prepared by dissolving 20 mass % of polyvinyl butyral in 80 mass % of butyl carbitol was added to the premixed liquid in an amount of 50 vol % based on the total volume of the ceramic aggregate and the pore former in the premixed liquid, and the components were mixed. After removing acetone (dispersion medium), the viscosity of the mixture was adjusted by appropriately adding butyl carbitol to obtain a measurement electrode protective layer paste used to manufacture the gas sensor elements No. 1 to No. 39.

TABLE 1

| Element No. | Measurement electrode protective layer preparation conditions | | | | Measurement electrode preparation conditions | | Properties of element | | | | |
|---|---|---|---|---|---|---|---|---|---|---|---|
| | Aggregate material for measurement electrode protective layer | Amount of Aggregate (vol %) | Amount of pore former (vol %) | Average particle size of pore former (μm) | Average particle size of pore former (μm) | Firing temperature (°C.) | B/A | Average pore size A of measurement electrode (μm) | Average pore size B of measurement electrode protective layer (μm) | Porosity of measurement electrode protective layer (%) | Thickness of measurement electrode protective layer (μm) |
| 1 | Yttria-partially stabilized zirconia | 90 | 10 | 0.05 | 3.5 | 1350 | 0.01 | 3.0 | 0.03 | 11 | 50 |
| 2 | Yttria-partially stabilized zirconia | 90 | 10 | 0.2 | 3.5 | 1350 | 0.05 | 3.0 | 0.15 | 11 | 50 |
| 3 | Yttria-partially stabilized zirconia | 90 | 10 | 0.3 | 3.5 | 1350 | 0.08 | 3.0 | 0.23 | 12 | 50 |
| 4 | Yttria-partially stabilized zirconia | 90 | 10 | 1.5 | 3.5 | 1350 | 0.33 | 3.0 | 1.0 | 14 | 50 |
| 5 | Yttria-partially stabilized zirconia | 90 | 10 | 2.8 | 3.5 | 1350 | 0.67 | 3.0 | 2.0 | 15 | 50 |
| 6 | Yttria-partially stabilized zirconia | 90 | 10 | 3.5 | 3.5 | 1350 | 0.90 | 3.0 | 2.7 | 15 | 50 |
| 7 | Yttria-partially stabilized zirconia | 90 | 10 | 4.1 | 3.5 | 1350 | 1.00 | 3.0 | 3.0 | 16 | 50 |
| 8 | Yttria-partially stabilized zirconia | 90 | 10 | 7 | 3.5 | 1350 | 1.70 | 3.0 | 5.1 | 21 | 50 |
| 9 | Yttria-partially stabilized zirconia | 100 | 0 | 1.5 | 3.5 | 1350 | 0.33 | 3.0 | 1.0 | 3 | 50 |
| 10 | Yttria-partially stabilized zirconia | 97 | 3 | 1.5 | 3.5 | 1350 | 0.37 | 3.0 | 1.1 | 5 | 50 |
| 11 | Yttria-partially stabilized zirconia | 40 | 60 | 1.5 | 3.5 | 1350 | 0.37 | 3.0 | 1.1 | 50 | 50 |
| 12 | Yttria-partially stabilized zirconia | 20 | 80 | 1.5 | 3.5 | 1350 | 0.33 | 3.0 | 1.0 | 65 | 50 |
| 13 | Yttria-partially stabilized zirconia | 90 | 10 | 0.05 | 0.8 | 1350 | 0.06 | 0.51 | 0.03 | 10 | 50 |
| 14 | Yttria-partially stabilized zirconia | 90 | 10 | 0.2 | 0.8 | 1350 | 0.20 | 0.51 | 0.10 | 14 | 50 |
| 15 | Yttria-partially stabilized zirconia | 90 | 10 | 10 | 20 | 1350 | 0.59 | 15 | 8.8 | 25 | 50 |
| 16 | Yttria-partially stabilized zirconia | 90 | 10 | 20 | 20 | 1350 | 0.79 | 15 | 11.9 | 23 | 50 |
| 17 | Yttria-partially stabilized zirconia | 90 | 10 | 0.2 | 0.4 | 1350 | 0.34 | 0.29 | 0.10 | 14 | 50 |
| 18 | Yttria-partially stabilized zirconia | 90 | 10 | 0.3 | 0.8 | 1350 | 0.29 | 0.51 | 0.15 | 15 | 50 |
| 19 | Yttria-partially stabilized zirconia | 90 | 10 | 4.1 | 12 | 1350 | 0.33 | 9.0 | 3.0 | 16 | 50 |
| 20 | Yttria-partially stabilized zirconia | 90 | 10 | 7 | 20 | 1350 | 0.34 | 15 | 5.1 | 21 | 50 |
| 21 | Yttria-partially stabilized zirconia | 90 | 10 | 10 | 30 | 1350 | 0.35 | 25 | 8.8 | 25 | 50 |

TABLE 2

| Element No. | Measurement electrode protective layer preparation conditions | | | | Measurement electrode preparation conditions | | Properties of element | | | | |
|---|---|---|---|---|---|---|---|---|---|---|---|
| | Aggregate material for measurement electrode protective layer | Amount of Aggregate (vol %) | Amount of pore former (vol %) | Average particle size of pore former (μm) | Average particle size of pore former (μm) | Firing temperature (°C.) | B/A | Average pore size A of measurement electrode (μm) | Average pore size B of measurement electrode protective layer (μm) | Porosity of measurement electrode protective layer (%) | Thickness of measurement electrode protective layer (μm) |
| 22 | Yttria-partially stabilized zirconia | 90 | 10 | 1.5 | 3.5 | 1350 | 0.33 | 3.0 | 1.0 | 14 | 5 |

TABLE 2-continued

| | Preparation conditions | | | | | Measurement electrode preparation conditions Average particle size of pore former (μm) | | Properties of element | | | |
|---|---|---|---|---|---|---|---|---|---|---|---|
| | Measurement electrode protective layer preparation conditions | | | | | | | | | | |
| Element No. | Aggregate material for measurement electrode protective layer | Amount of Aggregate (vol %) | Amount of pore former (vol %) | Average particle size of pore former (μm) | | Firing temperature (° C.) | B/A | Average pore size A of measurement electrode (μm) | Average pore size B of measurement electrode protective layer (μm) | Porosity of measurement electrode protective layer (%) | Thickness of measurement electrode protective layer (μm) |
| 23 | Yttria-partially stabilized zirconia | 90 | 10 | 1.5 | 3.5 | 1350 | 0.33 | 3.0 | 1.0 | 14 | 10 |
| 24 | Yttria-partially stabilized zirconia | 90 | 10 | 1.5 | 3.5 | 1350 | 0.33 | 3.0 | 1.0 | 14 | 100 |
| 25 | Yttria-partially stabilized zirconia | 90 | 10 | 1.5 | 35 | 1350 | 0.33 | 3.0 | 1.0 | 14 | 200 |
| 26 | Yttria-partially stabilized zirconia | 90 | 10 | 1.5 | 3.5 | 1350 | 0.33 | 3.0 | 1.0 | 14 | 300 |
| 27 | Yttria-stabilized zirconia | 90 | 10 | 1.5 | 3.5 | 1350 | 0.4 | 3.0 | 1.2 | 15 | 50 |
| 28 | Calcia-partially stabilized zirconia | 90 | 10 | 1.5 | 3.5 | 1350 | 0.37 | 3.0 | 1.1 | 13 | 50 |
| 29 | Calcia-stabilized zirconia | 90 | 10 | 1.5 | 3.5 | 1350 | 0.30 | 3.0 | 0.9 | 13 | 50 |
| 30 | α-Alumina | 90 | 10 | 1.5 | 3.5 | 1350 | 0.33 | 3.0 | 1 | 15 | 50 |
| 31 | $Al_2O_3 \cdot MgO$ spinel | 90 | 10 | 1.5 | 3.5 | 1350 | 0.27 | 3.0 | 0.8 | 17 | 50 |
| 32 | Mullite | 90 | 10 | 1.5 | 3.5 | 1350 | 0.40 | 3.0 | 1.2 | 16 | 50 |
| 33 | Cordierite | 90 | 10 | 1.5 | 3.5 | 1350 | 0.37 | 3.0 | 1.1 | 14 | 50 |
| 34 | Magnesia | 90 | 10 | 1.5 | 3.5 | 1350 | 0.47 | 3.0 | 1.4 | 19 | 50 |
| 35 | Yttria | 90 | 10 | 1.5 | 3.5 | 1350 | 0.43 | 3.0 | 1.3 | 19 | 50 |
| 36 | Yttria-partially stabilized zirconia | 90 | 10 | 1.5 | 3.5 | 1050 | 0.25 | 8.5 | 2.1 | 54 | 65 |
| 37 | Yttria-partially stabilized zirconia | 90 | 10 | 1.5 | 3.5 | 1200 | 0.45 | 3.3 | 1.5 | 20 | 50 |
| 38 | Yttria-partially stabilized zirconia | 90 | 10 | 1.5 | 3.5 | 1500 | 0.29 | 2.8 | 0.8 | 13 | 50 |
| 39 | Yttria-partially stabilized zirconia | 90 | 10 | 1.5 | 3.5 | 1650 | 0.07 | 1.5 | 0.1 | 3 | 45 |

Preparation of Measurement Electrode Paste

A pore former made of a melamine-formaldehyde condensate having a particle size shown in Tables 1 and 2 was added to a mixture of yttria-partially stabilized zirconia (30 mass %), platinum (40 mass %), and rhodium (40 mass %) in an amount of 30 vol % based on the total volume of yttria-partially stabilized zirconia, platinum, and rhodium to prepare a raw material powder. After the addition of a given amount of acetone (dispersion medium), the mixture was premixed to obtain a premixed liquid. An organic binder solution prepared by dissolving 20 mass % of polyvinyl butyral in 80 mass % of butyl carbitol was added to the premixed liquid in an amount of 50 vol % based on the total volume of yttria-partially stabilized zirconia, platinum, rhodium, and the pore former in the premixed liquid, and the components were mixed. After removing acetone (dispersion medium), the viscosity of the mixture was adjusted by appropriately adding butyl carbitol to obtain a measurement electrode paste used to manufacture the gas sensor elements No. 1 to No. 39.

Manufacturing of Gas Sensor Element

A gas sensor element having a structure shown in FIG. 1 was manufactured using the measurement electrode protective layer paste and the measurement electrode paste prepared as described above. Specifically, green sheets (unfired bodies) that respectively form the first substrate layer 1, the second substrate layer 2, the third substrate layer 3, the first solid electrolyte layer 4, the spacer layer 5, and the second solid electrolyte layer 6 upon firing were produced using zirconia as the solid electrolyte material firstly.

Next, the outer pump electrode 23 was printed on the upper surface of the green sheet (green sheet for second solid electrolyte layer) that forms the second solid electrolyte layer 6 upon firing using an electrode paste made of yttria-partially stabilized zirconia and platinum, and the inner pump electrode 22a and the auxiliary pump electrode 51b were printed on the under surface of the green sheet using the electrode paste together with wires connected to each electrode. The outer pump electrode protective layer (outer circumferential surface protective layer) 24 was further formed to cover the outer pump electrode 23 using an outer circumferential surface protective layer paste.

Likewise, the inner pump electrode 22b and the auxiliary pump electrode 51b were printed on the upper surface of the green sheet (green sheet for first solid electrolyte layer) that forms the first solid electrolyte layer 4 upon firing using the electrode paste with wires connected to each electrode, and the measurement electrode 44 was printed using the measurement electrode paste together with wires connected to the electrode. The measurement electrode protective layer 45 was then printed to cover the measurement electrode 44 using the measurement electrode protective layer paste. Moreover, the part of this green sheet was punched to form the reference gas introduction space 43.

Moreover, the part of the green sheet (green sheet for spacer layer) that forms the spacer layer 5 upon firing was punched to form the gas inlet 10, the first internal space 20, and the second internal space 40. An organic paste that includes a sublimation substance was printed on the parts of the upper surface and the under surface of this spacer layer in order to form slits for the first diffusion-controlled section 11, the second diffusion-controlled section 13, and the third diffusion-controlled section 30. The printed organic paste is burned down during firing to form the first diffusion-controlled section 11, the second diffusion-controlled section 13, and the third diffusion-controlled section 30.

Furthermore, the reference electrode 42 was printed on the upper surface of the green sheet (green sheet for third substrate layer) that forms the third substrate layer 3 upon firing using the electrode paste together with wires connected to the reference electrode 42. The air introduction layer 48 was then formed to cover the reference electrode 42 using an air introduction layer paste including a material (e.g., alumina) for the air introduction layer 48. The part of this green sheet was further punched to form the pressure diffusion hole 75.

Moreover, the heater insulating layer 74 was printed on the upper surface of the green sheet (green sheet for second substrate layer) that forms the second substrate layer 2 upon firing using a resistance heating element paste and an insulating layer paste including an alumina material or the like so that the heater insulating layer 74 covered the resistance heating element 72. The part of this green sheet was further punched to form the through-hole 73, and a heater wire was then formed.

Furthermore, the heater electrode 71 was printed on the under surface of the green sheet (green sheet for first substrate layer) that forms the first substrate layer 1 upon firing using a heater electrode paste. The part of this green sheet was further punched to form the through-hole 73, and a heater wire was then formed.

Subsequently, the green sheet for first substrate layer, the green sheet for second substrate layer, the green sheet for third substrate layer, the green sheet for first solid electrolyte layer, the green sheet for spacer layer, and the green sheet for second solid electrolyte layer were laminated, cut at the end, and fired at a firing temperature shown in Tables 1 and 2 for 5 hours to obtain the gas sensor elements No. 1 to No. 39. These gas sensor elements exhibits the properties shown in Tables 1 and 2 in the measurement electrode protective layer 45 and the measurement electrode 44.

Examples 1 to 5 and Comparative Examples 1 to 3

The gas sensor elements shown in Table 3 among the gas sensor elements No. 1 to No. 39 were subjected to a durability test by the following method to determine the sensitivity decrease rate in the durability test, the presence or absence of cracks in the measurement electrode protective layer and the measurement electrode, and the presence or absence of clogging of the measurement electrode protective layer and the measurement electrode. The results are shown in Table 3.

Gas Sensor Element Durability Test

The NOx sensitivity was measured in a NOx model gas (500 ppm) using each manufactured gas sensor element, and taken as the initial NOx sensitivity. After dropping 1 μL of an Mg ion-containing aqueous solution (Mg ion concentration: 5 mmol/L) into the gas inlet of the gas sensor element, the gas sensor element was allowed to stand for 1 minute, and then driven at 800° C. for 10 minutes. This cycle was repeated one hundred times (i.e., 100 μL of the Mg ion-containing aqueous solution was dropped in total). The NOx sensitivity was measured in the NOx model gas using the gas sensor element, and compared with the initial NOx sensitivity to calculate the sensitivity decrease rate. The gas sensor element was disassembled after the measurement to determine the presence or absence of cracks in the measurement electrode protective layer and the measurement electrode. The cross section (polished surface) of the measurement electrode, protective layer and the measurement electrode was subjected to electron probe micro-analysis (EPMA) to determine the presence or absence of clogging of the measurement electrode protective layer and the measurement electrode due to Mg compounds.

TABLE 3

| | | | Properties of element | | Element evaluation results | | | |
|---|---|---|---|---|---|---|---|---|
| | Element No. | B/A | Average pore size A of measurement electrode (μm) | Average pore size B of measurement electrode protective layer (μm) | Sensitivity decrease rate in durability test (%) | Clogging of measurement electrode protective layer | Clogging of measurement electrode | Cracks |
| Ex. 1 | 2 | 0.05 | 3.0 | 0.15 | 6 | None | None | None |
| Ex. 2 | 3 | 0.08 | 3.0 | 0.23 | 1 | None | None | None |
| Ex. 3 | 4 | 0.33 | 3.0 | 1.0 | 1 | None | None | None |
| Ex. 4 | 5 | 0.67 | 3.0 | 2.0 | 3 | None | None | None |
| Ex. 5 | 6 | 0.90 | 3.0 | 2.7 | 7 | None | None | None |
| Comp. Ex. 1 | 1 | 0.01 | 3.0 | 0.03 | 55 | Occurred | None | None |
| Comp. Ex. 2 | 7 | 1.00 | 3.0 | 3.0 | 17 | None | None | None |
| Comp. Ex. 3 | 8 | 1.70 | 3.0 | 5.1 | 46 | None | Occurred | None |

As shown in Table 3, the gas sensor elements No. 2 to No. 6 (Examples 1 to 5) in which the average pore size A of the measurement electrode and the average pore size B of the measurement electrode protective layer satisfy the relationship "0.05≤B/A≤0.9" showed a low sensitivity decrease rate in the durability test. In particular, the gas sensor element No. 4 (Example 3) in which the average pore size A of the measurement electrode and the average pore size B of the measurement electrode protective layer satisfy the relationship "0.1<B/A<0.65" showed a very low sensitivity decrease rate in the durability test (i.e., exhibited high durability). On the other hand, the gas sensor element No. 1 (Comparative Example 1) in which the ratio B/A was less than 0.05, and the gas sensor elements No. 7 and No. 8 (Comparative Examples 2 and 3) in which the ratio B/A exceeded 0.9 showed a very high sensitivity decrease rate in the durability test (i.e., exhibited poor durability).

Examples 6 to 8 and Comparative Examples 4 and 5

The gas sensor elements shown in Table 4 among the gas sensor elements No. 1 to No. 39 were subjected to the above durability test to determine the sensitivity decrease rate in the durability test, the presence or absence of cracks in the measurement electrode protective layer and the measurement electrode, and the presence or absence of clogging of the measurement electrode protective layer and the measurement electrode. The results are shown in Table 4.

element No. 9 (Comparative Example 4) in which the porosity of the measurement electrode protective layer was less than 5%. This is because the pores in the measurement electrode protective layer did not communicate, as a result the gas to be measured could not reach the measurement electrode. When using the gas sensor element No. 12 (Comparative Example 5) in which the porosity of the measurement electrode protective layer exceeded 50%, cracks were occurred in the measurement electrode protective layer since the strength of the measurement electrode protective layer was too low.

Examples 9 to 11 and Comparative Examples 6 and 7

The gas sensor elements shown in Table 5 among the gas sensor elements No. 1 to No. 39 were subjected to the above durability test to determine the sensitivity decrease rate in the durability test, the presence or absence of cracks in the measurement electrode protective layer and the measurement electrode, and the presence or absence of clogging of the measurement electrode protective layer and the measurement electrode. The results are shown in Table 5.

TABLE 4

| | | Properties of element | | Element evaluation results | | | |
|---|---|---|---|---|---|---|---|
| | Element No | B/A | Porosity of measurement electrode protective layer (%) | Sensitivity decrease rate in durability test (%) | Clogging of measurement electrode protective layer | Clogging of measurement electrode | Cracks |
| Ex. 6 | 10 | 0.37 | 5 | 3 | None | None | None |
| Ex. 7 | 4 | 0.33 | 14 | 1 | None | None | None |
| Ex. 8 | 11 | 0.37 | 50 | 0 | None | None | None |
| Comp. Ex. 4 | 9 | 0.33 | 3 | NOx could not be measured (pores did not communicate) | | | |
| Comp. Ex. 5 | 12 | 0.33 | 65 | — | — | — | Occurred |

As shown in Table 4, the gas sensor elements No. 10, No. 4, and No. 11 (Examples 6 to 8) in which the porosity of the measurement electrode protective layer was within 5 to 50% showed a low sensitivity decrease rate in the durability test (i.e., exhibited high durability). On the other hand, the NOx concentration could not be measured using the gas sensor

TABLE 5

| | | Properties of element | | Element evaluation results | | | |
|---|---|---|---|---|---|---|---|
| | Element No. | B/A | Average pore size B of measurement electrode protective layer (μm) | Sensitivity decrease rate in durability test (%) | Clogging of measurement electrode protective layer | Clogging of measurement electrode | Cracks |
| Ex. 9 | 14 | 0.20 | 0.10 | 3 | None | None | None |
| Ex. 10 | 4 | 0.33 | 1.0 | 1 | None | None | None |
| Ex. 11 | 15 | 0.59 | 8.8 | 5 | None | None | None |
| Comp. Ex. 6 | 13 | 0.06 | 0.03 | 52 | Occurred | None | None |
| Comp. Ex. 7 | 16 | 0.79 | 11.9 | 11 | None | None | Occurred |

As shown in Table 5, the gas sensor elements No. 14, No. 4, and No. 15 (Examples 9 to 11) in which the average pore size of the measurement electrode protective layer was within 0.05 to 9 μm showed a low sensitivity decrease rate in the durability test without generating cracks (i.e., exhibited high durability). On the other hand, when using the gas sensor element No. 13 (Comparative Example 6) in which the average pore size of the measurement electrode protective layer was less than 0.05 μm, the pores in the measurement electrode protective layer were clogged. As a result, the sensitivity decrease rate in the durability test significantly increased. When using the gas sensor element No. 16 (Comparative Example 7) in which the average pore size of the measurement electrode protective layer exceeded 9 μm, cracks were occurred in the measurement electrode protective layer since the strength of the measurement electrode protective layer was too low.

Examples 12 to 15 and Comparative Examples 8 and 9

The gas sensor elements shown in Table 6 among the gas sensor elements No. 1 to No. 39 were subjected to the above durability test to determine the sensitivity decrease rate in the durability test, the presence or absence of cracks in the measurement electrode protective layer and the measurement electrode, and the presence or absence of clogging of the measurement electrode protective layer and the measurement electrode. The results are shown in Table 6.

average pore size of the measurement electrode was within 0.5 to 15 μm showed a low sensitivity decrease rate in the durability test without generating cracks (i.e., exhibited high durability). On the other hand, the gas sensor element No. 17 (Comparative Example 8) in which the average pore size of the measurement electrode was less than 0.5 μm showed a high sensitivity decrease rate in the durability test (i.e., exhibited poor durability). When using the gas sensor element No. 21 (Comparative Example 9) in which the average pore size of the measurement electrode exceeded 15 μm, cracks were occurred in the measurement electrode since the strength of the measurement electrode was too low.

Examples 16 to 19 and Comparative Examples 10 and 11

The gas sensor elements shown in Table 7 among the gas sensor elements No. 1 to No. 39 were subjected to the above durability test to determine the sensitivity decrease rate in the durability test, the presence or absence of cracks in the measurement electrode protective layer and the measurement electrode, and the presence or absence of clogging of the measurement electrode protective layer and the measurement electrode. The results are shown in Table 7.

TABLE 6

| | | Properties of element | | Element evaluation results | | |
|---|---|---|---|---|---|---|
| Element No | B/A | Average pore size A of measurement electrode (μm) | Sensitivity decrease rate in durability test (%) | Clogging of measurement electrode protective layer | Clogging of measurement electrode | Cracks |
| Ex. 12 | 18 | 0.29 | 0.51 | 3 | None | None | None |
| Ex. 13 | 4 | 0.33 | 3.0 | 1 | None | None | None |
| Ex. 14 | 19 | 0.33 | 9.0 | 2 | None | None | None |
| Ex. 15 | 20 | 0.34 | 15 | 2 | None | None | None |
| Comp. Ex. 8 | 17 | 0.34 | 0.29 | 10 | None | None | None |
| Comp. Ex. 9 | 21 | 0.35 | 25 | — | — | — | Occurred |

As shown in Table 6, the gas sensor elements No. 18, No. 4, No. 19, and No. 20 (Examples 12 to 15) in which the

TABLE 7

| | | Properties of element | | Element evaluation results | | |
|---|---|---|---|---|---|---|
| Element No. | B/A | Thickness of measurement electrode protective layer (μm) | Sensitivity decrease rate in durability test (%) | Clogging of measurement electrode protective layer | Clogging of measurement electrode | Cracks |
| Ex. 16 | 23 | 0.33 | 10 | 5 | None | None | None |
| Ex. 17 | 4 | 0.33 | 50 | 1 | None | None | None |

TABLE 7-continued

|  | Element No. | B/A | Thickness of measurement electrode protective layer (μm) | Sensitivity decrease rate in durability test (%) | Clogging of measurement electrode protective layer | Clogging of measurement electrode | Cracks |
|---|---|---|---|---|---|---|---|
| Ex. 18 | 24 | 0.33 | 100 | 1 | None | None | None |
| Ex. 19 | 25 | 0.33 | 200 | 0 | None | None | None |
| Comp. Ex. 10 | 22 | 0.33 | 5 | 12 | None | None | None |
| Comp. Ex. 11 | 26 | 0.33 | 300 | — | — | — | Occurred |

As shown in Table 7, the gas sensor elements No. 23, No. 4, No. 24, and No. 25 (Examples 16 to 19) in which the thickness of the measurement electrode protective layer was within 10 to 200 μm showed a low sensitivity decrease rate in the durability test without generating cracks (i.e., exhibited high durability). On the other hand, the gas sensor element No. 22 (Comparative Example 10) in which the thickness of the measurement electrode protective layer was less than 10 μm showed a high sensitivity decrease rate in the durability test (i.e., exhibited poor durability). When using the gas sensor element No. 26 (Comparative Example 11) in which the thickness of the measurement electrode protective layer exceeded 200 μm, cracks were occurred in the measurement electrode protective layer.

Examples 20 to 29

The gas sensor elements shown in Table 8 among the gas sensor elements No. 1 to No 39 were subjected to the above durability test to determine the sensitivity decrease rate in the durability test, the presence or absence of cracks in the measurement electrode protective layer and the measurement electrode, and the presence or absence of clogging of the measurement electrode protective layer and the measurement electrode. The results are shown in Table 8.

As shown in Table 8, the gas sensor elements No. 4 and No. 27 to No. 35 (Examples 20 to 29) that differed in the material for the measurement electrode protective layer showed a low sensitivity decrease rate in the durability test without generating cracks (i.e., exhibited high durability).

Examples 30 to 32 and Comparative Examples 12 and 13

The gas sensor elements shown in Table 9 among the gas sensor elements No. 1 to No. 39 were subjected to the above durability test to determine the sensitivity decrease rate in the durability test, the presence or absence of cracks in the measurement electrode protective layer and the measurement electrode, and the presence or absence of clogging of the measurement electrode protective layer and the measurement electrode. The results are shown in Table 9.

TABLE 8

|  |  | Preparation conditions | | Properties of element | | | Element evaluation results | | | |
|---|---|---|---|---|---|---|---|---|---|---|
|  | Element No. | Material for measurement electrode protective layer | Firing temperature (° C.) | B/A | Average pore size B of measurement electrode protective layer (μm) | Porosity of measurement electrode protective layer (%) | Sensitivity decrease rate in durability test (%) | Clogging of measurement electrode protective layer | Clogging of measurement electrode | Cracks |
| Ex. 20 | 4 | Yttria-partially stabilized zirconia | 1350 | 0.33 | 1.0 | 14 | 1 | None | None | None |
| Ex. 21 | 27 | Yttria-stabilized zirconia | 1350 | 0.4 | 1.2 | 15 | 1 | None | None | None |
| Ex. 22 | 28 | Calcia-partially stabilized zirconia | 1350 | 0.37 | 1.1 | 13 | 1 | None | None | None |
| Ex. 23 | 29 | Calcia-stabilized zirconia | 1350 | 0.30 | 0.9 | 13 | 2 | None | None | None |
| Ex. 24 | 30 | α-Alumina | 1350 | 0.33 | 1 | 15 | 1 | None | None | None |
| Ex. 25 | 31 | $Al_2O_3 \cdot MgO$ spinel | 1350 | 0.27 | 0.8 | 17 | 1 | None | None | None |
| Ex. 26 | 32 | Mullite | 1350 | 0.40 | 1.2 | 16 | 1 | None | None | None |
| Ex. 27 | 33 | Cordierite | 1350 | 0.37 | 1.1 | 14 | 2 | None | None | None |
| Ex. 28 | 34 | Magnesia | 1350 | 0.47 | 1.4 | 19 | 2 | None | None | None |
| Ex. 29 | 35 | Yttria | 1350 | 0.43 | 1.3 | 19 | 3 | None | None | None |

TABLE 9

| | | Preparation conditions Firing temperature (° C.) | | Properties of element | | | | Element evaluation results | | | |
|---|---|---|---|---|---|---|---|---|---|---|---|
| | Element No. | | B/A | Average pore size A of measurement electrode (μm) | Average pore size B of measurement electrode protective layer (μm) | Porosity of measurement electrode protective layer (%) | Thickness measurement electrode protective layer (μm) | Sensitivity decrease rate in durability test | Clogging of measurement electrode protective layer | Clogging of measurement electrode | Cracks |
| Ex. 30 | 37 | 1200 | 0.45 | 3.3 | 1.5 | 20 | 50 | 1 | None | None | None |
| Ex. 31 | 4 | 1350 | 0.33 | 3.0 | 1.0 | 14 | 50 | 1 | None | None | None |
| Ex. 32 | 38 | 1500 | 0.29 | 2.8 | 0.8 | 13 | 50 | 2 | None | None | None |
| Comp. Ex. 12 | 36 | 1050 | 0.25 | 8.5 | 2.1 | 54 | 65 | — | — | — | Occurred |
| Comp. Ex. 13 | 39 | 1650 | 0.07 | 1.5 | 0.1 | 3 | 45 | NOx could not be measured (pores did not communicate) | | | |

As shown in Table 9, the gas sensor elements No. 37, No. 4, and No. 38 (Examples 30 to 32) manufactured at a firing temperature within 1200 to 1500° C. showed a low sensitivity decrease rate in the durability test without generating cracks (i.e., exhibited high durability). On the other hand, when using the gas sensor element No. 36 (Comparative Example 12) manufactured at a firing temperature of less than 1200° C., cracks were occurred in the measurement electrode protective layer since the measurement electrode protective layer had insufficient strength due to insufficient sintering. When using the gas sensor element No. 39 (Comparative Example 13) manufactured at a firing temperature of more than 1500° C., the pores in the measurement electrode protective layer did not communicate due to excessive sintering. As a result, the NOx concentration could not be measured since the gas to be measured could not reach the measurement electrode.

The above gas sensor element and the method of manufacturing the same may suitably be used to measure the concentration of a specific gas component in the gas to be measured.

What is claimed is:

1. A gas sensor element being used to measure the concentration of a specific gas component in a gas to be measured, and including:
   a base member comprising a plurality of laminated solid electrolyte layers, and having a space that communicates with the outside of the gas sensor element and allows introduction of the gas to be measured into the gas sensor element; and
   three diffusion control sections positioned inside a space between a gas inlet and a porous measurement electrode,
   wherein the porous measurement electrode is formed on a surface of the space inside the base member, and is covered with a porous measurement electrode protective layer that acts as a fourth diffusion control section,
   wherein an average pore size A of the measurement electrode and an average pore size B of the measurement electrode protective layer satisfy the relationship "0.05≤B/A≤0.9"; the measurement electrode has an average pore size of 0.5 to 15 μm; and the measurement electrode protective layer has an average pore size of 0.05 to 9 μm, a porosity of 5 to 50%, and a thickness of 10 to 200 μm.

2. The gas sensor element according to claim 1, wherein the average pore size A of the measurement electrode and the average pore size B of the measurement electrode protective layer satisfy the relationship "0.1<B/A<0.65".

3. The gas sensor element according to claim 1, wherein the measurement electrode protective layer is made of at least one material selected from the group consisting of yttria-partially stabilized zirconia, calcia-partially stabilized zirconia, yttria-stabilized zirconia, calcia-stabilized zirconia, α-alumina, $Al_2O_3 \cdot MgO$ spinel, mullite, yttria, magnesia, and cordierite.

4. The gas sensor element according to claim 2, wherein the measurement electrode protective layer is made of at least one material selected from the group consisting of yttria-partially stabilized zirconia, calcia-partially stabilized zirconia, yttria-stabilized zirconia, calcia-stabilized zirconia, α-alumina, $Al_2O_3 \cdot MgO$ spinel, mullite, yttria, magnesia, and cordierite.

5. A method of manufacturing the gas sensor element according to claim 1, the method including:
   printing the measurement electrode on a surface of an unfired body of a base member, which forms solid layers when fired, using a measurement electrode paste that includes a constituent material for the measurement electrode, and printing the measurement electrode protective layer on the unfired body to cover the measurement electrode using a measurement electrode protective layer paste that includes a ceramic aggregate and a pore former to form a printed laminate body; and
   firing the printed laminate body,
   wherein the printed laminate body is fired at 1200 to 1500° C.

6. The method according to claim 5, wherein the measurement electrode paste includes a pore former.

7. The method according to claim 5, wherein the ceramic aggregate included in the measurement electrode protective layer paste is at least one type of ceramic particles selected from the group consisting of yttria-partially stabilized zirconia, calcia-partially stabilized zirconia, yttria-stabilized zirconia, calcia-stabilized zirconia, α-alumina, $Al_2O_3 \cdot MgO$ spinel, mullite, yttria, magnesia, and cordierite.

8. The method according to claim 5, wherein the average pore size A of the measurement electrode and the average pore size B of the measurement electrode protective layer satisfy the relationship "0.1<B/A<0.65".

9. The gas sensor according to claim 1, further comprising an outer pump electrode that is covered with an outer pump electrode protective layer formed of a porous body.

* * * * *